United States Patent
LaBelle

(10) Patent No.: US 12,292,768 B2
(45) Date of Patent: *May 6, 2025

(54) SYSTEM FOR BIOMECHANICALLY OPTIMIZING USE OF MOBILE DEVICES

(71) Applicant: UpBright LLC, Simpsonville, SC (US)

(72) Inventor: Shawn LaBelle, Simpsonville, SC (US)

(73) Assignee: UpBright LLC, Simpsonville, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/425,191

(22) Filed: Jan. 29, 2024

(65) Prior Publication Data

US 2024/0168527 A1    May 23, 2024

Related U.S. Application Data

(63) Continuation of application No. 18/330,981, filed on Jun. 7, 2023, now Pat. No. 11,927,993.

(60) Provisional application No. 63/354,739, filed on Jun. 23, 2022.

(51) Int. Cl.
    *G06F 1/16*    (2006.01)
    *G06F 1/3218*    (2019.01)

(52) U.S. Cl.
    CPC .......... *G06F 1/1694* (2013.01); *G06F 1/3218* (2013.01); *G06F 2200/1637* (2013.01)

(58) Field of Classification Search
    CPC .................................................. G06F 3/04162
    See application file for complete search history.

(56) References Cited

U.S. PATENT DOCUMENTS

| 10,563,373 | B1 | 2/2020 | Friesen |
| 10,602,976 | B2 | 3/2020 | Cunico et al. |
| 2013/0072820 | A1* | 3/2013 | Lee .......................... G16Z 99/00 600/594 |
| 2013/0314210 | A1 | 11/2013 | Schoner et al. |
| 2016/0262688 | A1* | 9/2016 | Nichols ................ A61B 5/0024 |
| 2017/0347965 | A1 | 12/2017 | Elhawary et al. |
| 2019/0038215 | A1* | 2/2019 | Cunico ................ A61B 5/7278 |
| 2020/0012410 | A1* | 1/2020 | Peng .................... G06F 3/04842 |

(Continued)

FOREIGN PATENT DOCUMENTS

WO    2018204769    8/2018

OTHER PUBLICATIONS

Thomas J. Law, 19 Ecommerce Statistics You Need to Know in 2023, blog article, Nov. 7, 2022, 20pp., Oberlo, Lithuania.

*Primary Examiner* — Chun-Nan Lin
(74) *Attorney, Agent, or Firm* — Kim and Lahey Law Firm, LLC; Douglas W. Kim; Hunter S. Freeman

(57) ABSTRACT

A biomechanically optimizing mobile device use system having a mobile computer device with readable storage and a display; an orientation determination system included with the mobile device and adapted to determine a position of the mobile device; and, an operating system that, when the mobile device is powered on and upon each repositioning of the mobile device, is adapted to: determine a current position, determine a reference position relative to one of a vertical position and a face down position, determine a stress angle of the mobile device according to a difference between the current position and the reference position, and, actuate a user notification according to a determination that the stress angle exceeds a predetermined angle for a predetermined length of time.

15 Claims, 8 Drawing Sheets

(56) References Cited

U.S. PATENT DOCUMENTS

2020/0094138 A1\* 3/2020 Chen .................. H04N 13/239
2020/0174517 A1 6/2020 Martinez et al.

\* cited by examiner

SYSTEM FOR BIOMECHANICALLY OPTIMIZING USE OF MOBILE DEVICES

RELATED APPLICATION

This application is a continuation of U.S. patent application Ser. No. 18/330,981 filed Jun. 7, 2023 and incorporated by reference.

BACKGROUND OF THE INVENTION

1) Field of the Invention

This invention is directed to the detection and notification of aggravation of muscular pain in the head, neck, and spine due to the changes in the natural head weight bearing ability of the body resulting from improper positioning of the head and neck due to using or viewing mobile devices. Included in this functionality is the improvement to the analysis of the weight-bearing ability of the head and the negative effects brought upon improperly positioning of the head. The primary function of this invention is to modify the user's behavior in using the mobile device to reduce the strain on the body caused by long periods of use.

2) Description of the Related Art

Posture, when used to describe the human body, is the position of the body in relation to gravity when standing, sitting, and laying. It is known that having a good posture ensures that the body is symmetrical in alignment and that the muscular tension is correct. Good posture involves training your body to stand, walk, bend, sit, and lay in a manner where the least amount of pressure is placed on muscles and ligaments when stationary, moving, or performing exercise activities. Benefits of a good posture include keeping bones and joints properly aligned, reducing stress on the body, reducing wear on joints, muscles, nerves, and ligaments, preventing neck, back, and muscle pain, reducing the risk of muscular fatigue, preventing the spine from becoming fixed into abnormal positions and reducing unnecessary pressure on the nerves and ligaments of the neck and spine.

When the head is in an upright position (defined by the ear being over the shoulders when viewed from the side), the neck muscles and ligaments are balanced and do not create abnormal tension of the muscles or nerves. Even a lightweight mobile device gets heavy with extended use, increased mobile device use has caused users to spend more time with their head in a forward and flexed position. This causes the relative weight of the head to shift forward. Over time this causes the head to shift more forward at rest. This phenomenon has been called "Forward Head Posture." When the head moves forward, the head loses the support of the spinal column and now the head feels like it weighs more, dependent on how far forward the head rests. For example, a 12-pound head can feel much like a 60-pound head when the head is flexed forward to 60 degrees. Studies have shown that the position of the head forward also causes increased muscle activity of the muscles in the back of the neck that connect the skull to the upper back, especially the upper trapezius, erector spinae and neck extensor muscles. This leads to pain, stiffness and burning in those muscles from overuse. Furthermore, as the head moves forward over prolonged periods, the increased weight increases ligament lengthening in the back of the neck, while also shortening the ligaments in the front of the neck. Ligaments are designed in layers or 'laminations.' The nature of these laminations of ligament causes load placed on them to be translated at a slower than expected rate. This phenomenon, known as 'hysteresis,' causes the ligament to elongate or shorten at a slower rate than expected. The overlap of the tissues allows for a unique combination of a strong response to abrupt pulling forces, while also allowing for slow elongation over time for slow pulling forces. This is known as ligament 'creep'. As load is placed on the ligament, it retains an initial elastic response. After a period of time, (typically 5 minutes or more, but is also dependent on the length and thickness of the ligament) the ligament begins to deform or lengthen. When someone uses a mobile device and the head is held forward for extended periods of time (greater than 5 minutes), the neck ligaments deform to shorten in the front and lengthen in the back. The neck muscles in the back become fatigued and can begin to contract, firing off mechanoreceptors, nerve sensors that relay positional sense back to the brain. This can cause contraction and spasm of the head, jaw, neck and shoulder muscles as well as the localized blood vessels, which are also under muscular control. This, in turn can fire off nociceptors, (pain sensors) which can lead to headaches, as well as pain in the neck, shoulder, jaw and arms. This can also lead to a loss of perception of normal head placement, further allowing the users head to flex forward. This can also lead to balance dysfunction. Furthermore, this forward head position causes flexion of the upper thorax and can lessen normal lung function. This cascading effect has been described as "Tech Neck." As of January 2023, nearly 7 billion smart phones are in use worldwide. The wide acceptance of the smart phone, tablet, and other mobile devices has created patterns of use that result in "Tech Neck."

It has been suggested that for viewing smart phones and other mobile devices, that the user should develop proper posture and neck alignment by positioning the body so that a straight vertical line can be imposed from the ear to the shoulder. While most users tilt their chin down to read a mobile device, this is not optimal. The user should raise the device to eye level so that the head isn't perpetually dropping; an action which can result in muscle strain and injury.

Attempts to monitor and correct improper posture have been tried such as Cunico et al. (U.S. Pat. No. 10,602, 976B2). In Cunico et al. a machine implemented method is provided for minimizing effects of incorrect posture of the user. This system relies on a second device with a camera to measure a "posture quotient" of an individual. Once the "posture quotient" is determined that indicates improper posture, possible actions may be taken that would reinforce proper posture. An external system can also be used to collect the data ("posture quotient", remediation and results) upon which to perform analysis.

In another attempt to enforce proper posture, Moeller (U.S. Pat. No. 10,453,373 B2). measures the angle of the device to infer improper posture. In Moeller the measuring application is separate and distinct from the operating system. This requires independent installation of the application by the user. Furthermore, the application "obfuscates" the screen overlaying notices over other applications. This complicates interactions with other applications increasing the probability of unintended results by user interaction. Further, the separate application requires independent maintenance action and a subscription service to ensure updates.

Having a device that can detect a potentially harmful motion or position, prior to or soon after such motion or position occurs, would be advantageous.

It would also be advantageous if such device was integrated into the mobile device use of which typically leads to potentially harmful motion or position.

It would also be advantageous for a system to be able to monitor, record, and report potentially harmful motions or positions of an individual.

It would also be advantageous for a system to be able to monitor, record, and report potentially harmful motions or positions of an individual and provide feedback that seeks to reduce such motions or positions.

It would also be advantageous for such a system to be integrated with the operating system of the user device to facilitate ease of installation, maintenance, and interactions.

BRIEF SUMMARY OF THE INVENTION

The above objectives are accomplished by providing a system for biomechanically optimizing mobile device use through position detection and notification; said system comprising: a mobile device having a computer readable storage and a display; a processor included in the mobile device and an electrical communication with the computer readable storage and the display; an orientation determination system included with the mobile device and adapted to determine a position of the mobile device; and, an operating system stored on the computer readable storage that, when the mobile device is powered on, is adapted to: determine a reference position relative to one of a vertical position and a horizontal (i.e. face down) position, determine a stress angle of the mobile device according to a difference between the position and the reference position, and, actuate a user notification according to a determination that the stress angle exceeds a predetermined angle for a predetermined length of time.

In one embodiment of the invention, the system includes a time determining system within the mobile device operating system adapted to determine an actual length of time that the mobile device is held in a position that the stress angle exceeds the predetermined angle. In one embodiment the system can determine a current position upon powering on and compare the same against the reference position and calculate a stress angle according to the difference between the current position and the reference position.

The orientation determination system may be adapted to determine a movement of the mobile device and the operating system may be adapted to determine a stress angle according to a determination that the movement occurred. The predetermined angle and predetermined length of time may be stored in memory, user configurable, remotely configurable, or any combination. The reference position may be set relative to the horizontal position, the vertical position, or any combination. The reference position may be in a plus or minus range, such as 5 degrees plus or minus, stored in memory, user configurable, remotely configurable, or any combination.

The operating system may be adapted to generate and transmit the user notification on the mobile device when the operating system determines that the stress angle exceeds the predetermined angle for a predetermined length of time. The system may be adapted or configured to generate any number of notices based on continued detection of a stress angle. Notifications may include dimming the display, actuating a haptic system, actuating an audio system, displaying a visual notification on the display, suspending an operation of other currently running applications, and any combination thereof. The operating system may be adapted to actuate the user notification for a predetermined activation period of time. The operating system may be adapted to stop the user notification and return the mobile device to an initial state according to the stress angle being less than the predetermined angle for a recovery period of time. The operating system may be adapted to reduce the predetermined length of time according to the number of times the stress angle has exceeded the predetermined angle. The operating system may be adapted to increase the activation period of time according to the number of times the stress angle exceeds the predetermined angle, the size of the stress angle, or a combination.

The system can include a mobile device having a computer readable storage and a display; a processor included in the mobile device and in communication with the computer readable storage and the display; an orientation determination system included with the mobile device and adapted to determine a position of the mobile device; and, an operating system stored on the computer readable storage that, when the mobile device is powered on, is adapted to: determine a reference position relative to one of a vertical position and a horizontal (i.e. face down) position, determine a stress angle of the mobile device according to a difference between the position and the reference position, and, actuate a user notification according to a determination that the stress angle exceeds a predetermined angle. The operating system can be adapted to determine an actual length of time that the mobile device is held in the position according to the time determining system and determine a movement of the mobile device and the operating system is adapted to determine a stress angle according to a determination that the movement occurred. The predetermined angle and predetermined length of time can be retrieved from the computer readable storage. The predetermined angle and the predetermined length of time can be user configurable. The reference position is in a range of 5 degrees plus or minus from the vertical position or a horizontal position. The operating system can be adapted to generate and transmit the user notification on the mobile device when the operating system determines that the stress angle exceeds the predetermined angle for a predetermined length of time. The user notification can be a first user notification, and the operating system can be adapted to, after generating the first user notification, generate a second or subsequent user notification when the stress angle is continued for a set of subsequent predetermined period of time. The second or subsequent user notification can include an effect taken from the group consisting of dimming the display, actuating a haptic system, actuating an audio system, displaying a visual notification on the display, and any combination thereof. The second user notification can be the same notification that is activated for a different period of time or for a difference intensity. The predetermined angle can be 5 degrees or greater and 15 degrees or greater. The operating system can be adapted to stop the user notification and return the mobile device to an initial state according to the stress angle being less than the predetermined angle for a recovery period of time.

The system can include a user notification that is sent to an executing application on the mobile device adapted to suspend an operation of an application currently running on the mobile device. The operating system can be adapted to determine the stress angle upon a detection of movement of the mobile device from the current position. The operating system can be adapted to reduce the predetermined length of time according to a number of times the stress angle exceeds the predetermined angle. The operating system can be adapted to actuate the user notification for a predetermined activation period of time. The operating system can be adapted to increase the activation period of time according to a number of times the stress angle exceeds the predetermined angle.

The system can include an operating system adapted to increase the user activation period of time according to a size of the stress angle. The operating system can be adapted to actuate a user notification according to the stress angle exceeding a predetermined angle for a predetermined period of time. The predetermined period of time is greater than 4 seconds and can be greater than 15 seconds. The reference position can be in a range relative from one or a vertical plane and a horizontal plane and retrieved from the computer readable medium. The operating system can be adapted to dim the display in increasing increments the longer the stress angle exceeds the predetermined angle.

BRIEF DESCRIPTION OF THE SEVERAL VIEWS OF THE DRAWINGS

The construction designed to carry out the invention will hereinafter be described together with other features thereof. The invention will be more readily understood from reading the following specification and by reference to the accompanying drawings forming a part thereof, wherein an example of the invention is shown and wherein.

DETAILED DESCRIPTION OF THE INVENTION

With reference to the drawings, the invention for biomechanically optimizing mobile device use will now be described in more detail. This system, including its implementation in an operating system, improves the current hardware and software of mobile devices. Currently, mobile devices has led to "tech neck" which can be reduced or eliminated by implementation of the present system. In fact, the current operation of mobile devices created the solution that this present system solves. The process and machine that is used in the system such as hardware and an operating system stored and executed by the hardware provides the improvements of the present system.

Figure 1:
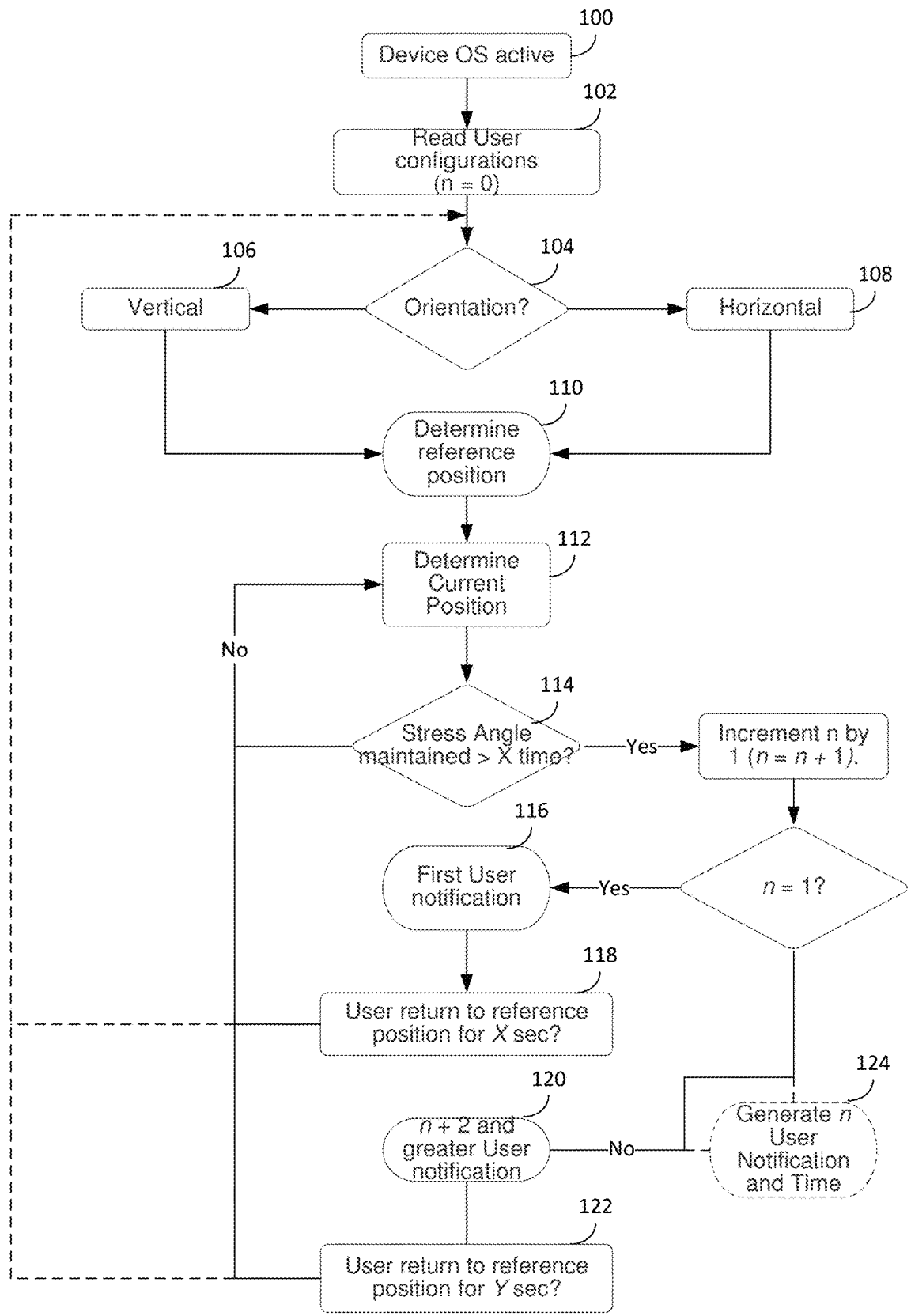
FIG. 1 is flowchart illustrating certain functionality of the system.

Referring to FIG. 1, the operating system and the processes, operations, and functionality that is achieved by the related hardware and software is shown. An operating system is the machine-readable language that supports computer functions such as executing applications and controlling hardware. The operating system can be included in a mobile device so that the operating system is activated at 100 when the mobile device is powered on. This embodiment does not require the user to activate an application. The operating system can have a background component that initiates upon powering of the mobile device or can be activated by the user. The background component can run with or without the user interface or otherwise with a user notification. Therefore, the operating system can capture information, receive input, and store information without the need for executing an application. The operating system can access a set of user configurations in respect to position, time, cycle iterations and other user preferences at 102.

The operating system can receive input from components of the mobile device such as the camera, magnetic field sensors, gravity sensors, location sensors (e.g., GPS receiver), accelerometers, timing device, and any combination. These inputs can be passed to an orientation determination system to determine the special orientation of the mobile device relative to the ground or the user. In a preferred embodiment, the inputs can be used to determine the positional orientation 104 of the device, where horizontal 108 is parallel to the plane of the horizon and vertical 106 is at a right angle to the horizontal 108 plane. In the vertical position 106 the user may be standing, sitting, leaning, or any combination with the spine generally perpendicular to the horizon. In the horizontal position 108, or the face down position, the user may be laying, reclining, or any similar position where the spine is approximately parallel to the horizon. Once the device determines the vertical or horizontal orientation a reference position is established at 110. The reference position is the benchmark position for proper angling of the device which all future measurements can be compared against until a new reference position is set. Additional readings may be taken from time to time to determine a current position of the mobile device as of the readings, and such readings may be triggered by a change in the orientation of the device or other movement.

One or more inputs can be used to determine if a proper device position is maintained at 114 by comparison of inputs to the reference position determined at 110 and the current position determined at 112. Detection of an improper device position relative to the reference position indicates the user of the mobile device is in a potentially disadvantageous or harmful position or motion. In one embodiment, the present position of the device can be compared to the reference position to determine if the device is not within an allowable tolerance of the reference position. When outside of tolerance, the device is held at a stress angle where the user's head is likely positioned forward of the spine causing stress to the muscles and ligaments of the neck, head, and spine. In one embodiment the operating system can determine that the mobile device is tilted at a predetermined angle. Such predetermined angle can be 10 degrees or more relative to vertical, or otherwise indicated that the neck of the user is pointed downward at an undesirable angle, e.g., a stress angle. In a further embodiment the angle can be 5 degrees or more. In another embodiment, the predetermined angle can be 5 degrees or more from the horizontal, indicating the neck of the user is tilted with the chin pointed towards the chest, e.g., a stress angel. In one embodiment, position 112 supports a determination that the angular difference between the current position and the reference position exceeds the stress angle indicating the position of the mobile device is harmful to the user. The operating system can determine when an improper device position is maintained, the date, time, location, duration, and magnitude and compare the duration against a predetermined threshold at 114.

Based upon the determination at 114, the operating system can activate a user notification (e.g., reaction or response) at 116. If so, the user notification can be used to give a notification to the user. The user notification can take several forms such as dimming the screen of the mobile device, obscuring the screen, flashing the screen or other light of the mobile device, emit an audible signal, actuate a haptic assembly (e.g., vibrate or other feedback), as well as any combination. The user notification can be activated by the operating system that communicates with the mobile device hardware to change the appearance of the screen. The appearance of the screen can be modified through the operating system and can control the hardware directly such as drivers that are in communication with an operating system layer. This notification informs the user that the motion or position of the device should be changed or is undesirable.

When a notification occurs, the user can respond by modifying the motion or position of the device. The operating system can detect and record such modification including the date, time, duration, and time from notification to modification, characteristics of the modification and any combination. For example, the user can tilt the mobile device upward (typically straightening the neck) in response to the notification. Upon detecting modification of sufficient measurement for a recovery period of time of sufficient duration, the operating system can remove the user notification at 118. In one embodiment, the device is then return to the determination of orientation 104. A recovery period of time is the time interval necessary for the muscles to recover, ligaments to relax, and the body to generally recover from a stress angle. If the user continues to hold the device in a position that exceeds the predetermined angle for a user configured predetermined length of time (e.g., threshold time), a second or subsequent user notifications can be sent at 120. This cycle can be repeated with subsequent user notifications of continued failure to modify the device to an orientation within the predetermined angle repeated again at 124 when the predetermined length of time is again exceeded Thereafter the cycle from 112 to 124 can be repeated again ad infinitum. Removal of notification occurs upon modification of the device position at 122 and the sequence can return to orientation 104. Such functionality requires a time determining system comprising a means to record initial tilt exceeding the predetermined angle, a means to record duration of time during which the tilt of the device exceeds the predetermined angle, a means to reset the duration when the tilt is returned to an angle within the predetermined angle, and a means to prompt user notification and reset the duration.

Figure 2:
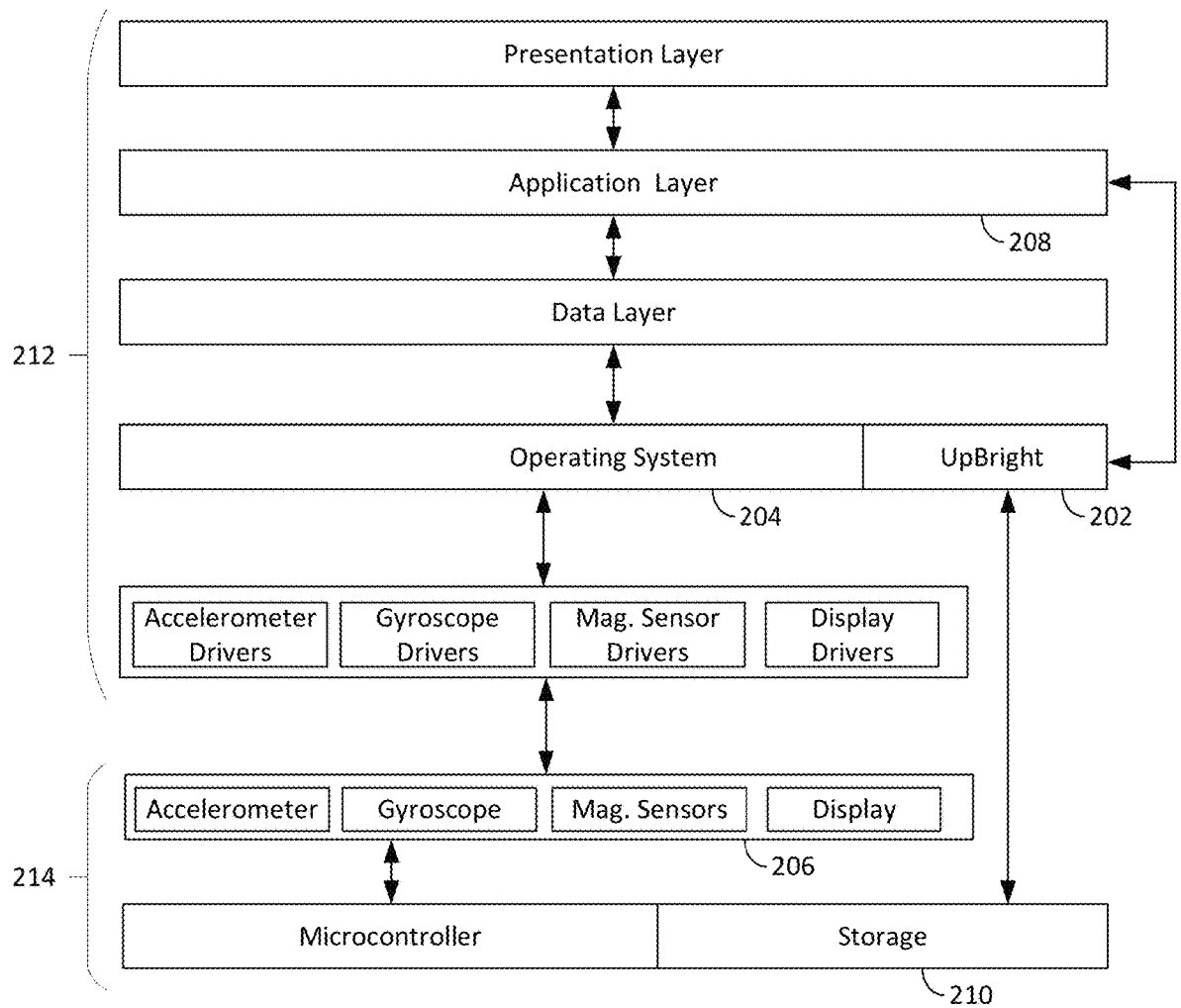
FIG. 2 is schematic illustrating the hardware and software layers and processes and operations of the system.

Referring to FIG. 2, computer readable instructions 202 can be included at the operating system layer 204 so that the computer readable instructions are loaded and operating when the mobile device is powered on. The operating system layer 204 can access computer readable storage 210 and user saved preferences. The operating system can use sensors 206 to detect orientation and determine an initial position or state that is an acceptable position of the mobile device. The operating system can determine when the mobile device's position changes. This determination can be made without regard to the current applications that may be running on application layer 208. The operating system can determine that a notification is required and provide this information to any application that may be running. The notification can occur regardless of any application running as it can be determined at the operating system layer if the change in position of the mobile device warrants a notification. Because the position of the mobile device can be determined at the operating layer, the functionality of the present system does not rely upon an application, and each running application can be informed of the modifications to the mobile device, such as the screen dimming, and respond accordingly. In one embodiment, the computer readable instructions can be included in operating system 212 and executed by hardware 214. It should be noted that one or more layers, as illustrated, can be added or omitted.

Figure 3:
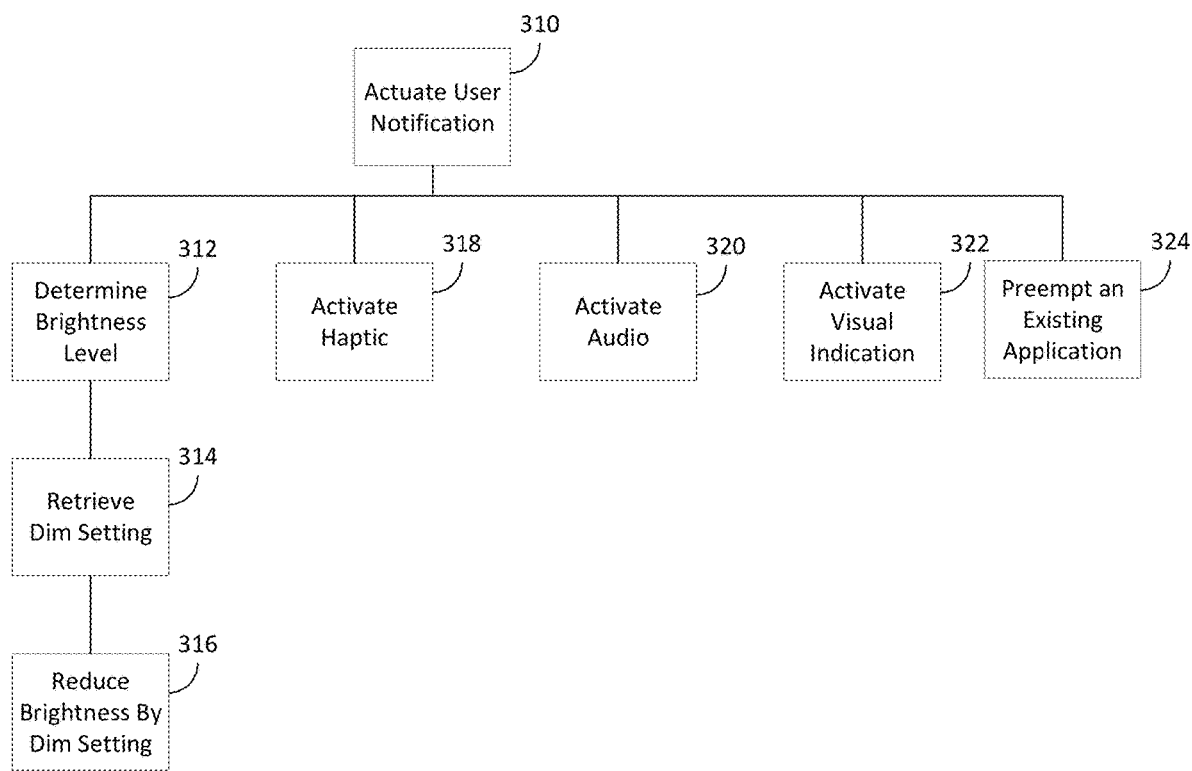
FIG. 3 is a graphical representation of the operation and processes of the system implemented with software and hardware.

Referring to FIG. 3. The user notification 310 can include a dimming effect accomplished by determining the current screen brightness level of the mobile device at 312, retrieving the notification parameters at 314 and applying the notification at 316. For example, the operating system can determine that the current screen brightness level is 80%, retrieve that the notification is to dim the screen down to 75% of the current brightness level and reduce the brightness to 60% (on a 0 to 100 scale—60% of 80%). The notification can be haptic at 318, audible at 320, visual at 322, and preempt or override the appearance of an executing application at 324 and any combination. In one embodiment, notification may include interruption or termination of one or more user applications. In one embodiment, the system can compare notification events and based upon the increase or decrease in frequency of notifications, amplify, or reduce the effect. For example, if the system is set to actuate notification 5 seconds after the detecting of improper position, multiple notifications can result in the actuation time being lowered to, for example, 3 seconds. Therefore, the user's behavior has a higher chance of being modified. The modifications to the notification can include volume, brightness, time between trigger and effect, time of the effect, and any other modifications to notifications to alert the user to practice proper posture. In one embodiment, the duration of the notification can be based on a predetermined activation period of time which may be programmed into the system, user configurable, remotely configurable, or any combination.

Figure 4A:
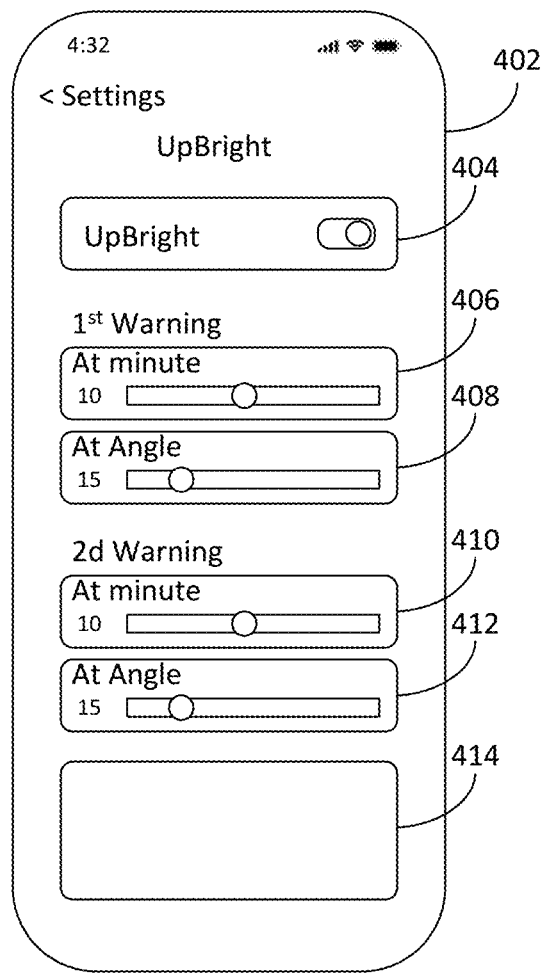
FIG. 4A is a schematic of aspects of the hardware and user interface of the system.

Referring to FIG. 4A, the user configurable controls of the mobile device 402 can include: a setting to discontinue use of the notification system at 404; set the initial user notification time, e.g., the predetermined length of time, at 406 and angle, e.g., the predetermined angle, at 408; set subsequent notification times at 410 and angles at 412 and personalize the notifications at 414.

Figure 4B:
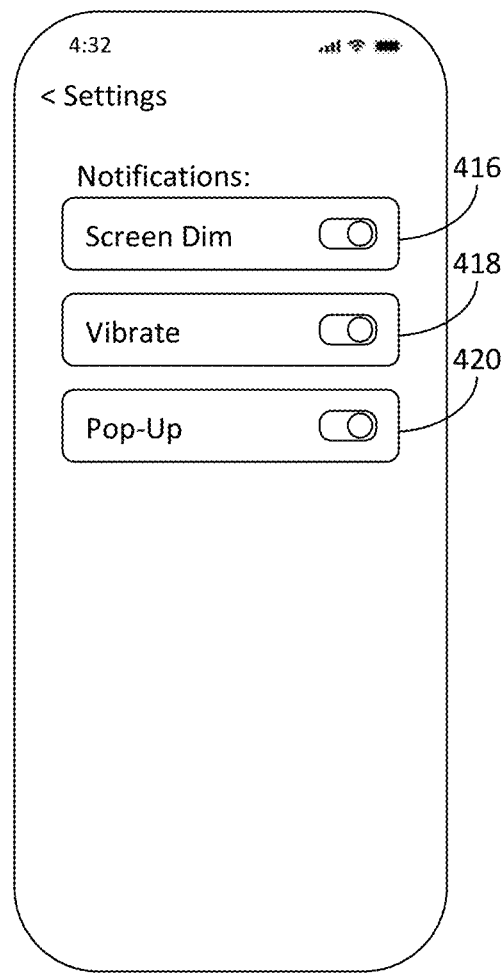
FIG. 4B is a schematic of aspects of the hardware and user interface of the system.

Referring to FIG. 4B, further user configurable controls of the mobile device 402 can include selecting notifications such as toggles for dimming the screen at 416, vibration at 418, and pop-up notifications at 420. Further user-configured controls are possible including more detailed controls of notification, warning settings, etc.

Figure 5A:
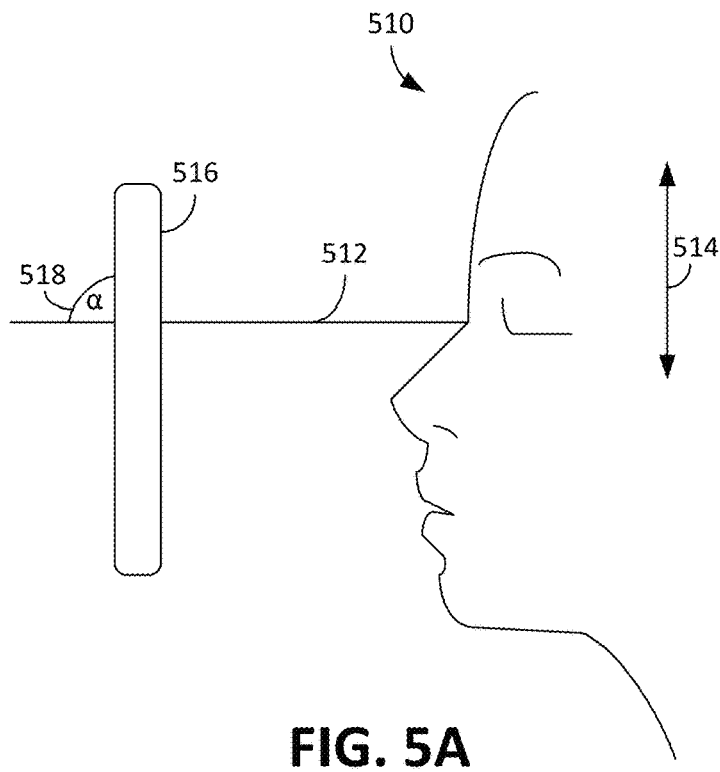
FIG. 5A is schematic of aspects of the functionality of the system.

Referring to FIG. 5A, user 510 aligns the head vertically so that the line of sight 512 is generally parallel to plane 516. This position places the head at about a 90-degree angle vertically as compared with plane 514. The mobile device 516 is advantageously held at about a 90-degree angle to horizontal as shown by angle 518. FIG. 5A is an example of proper posture generally healthy for the user.

Figure 5B:
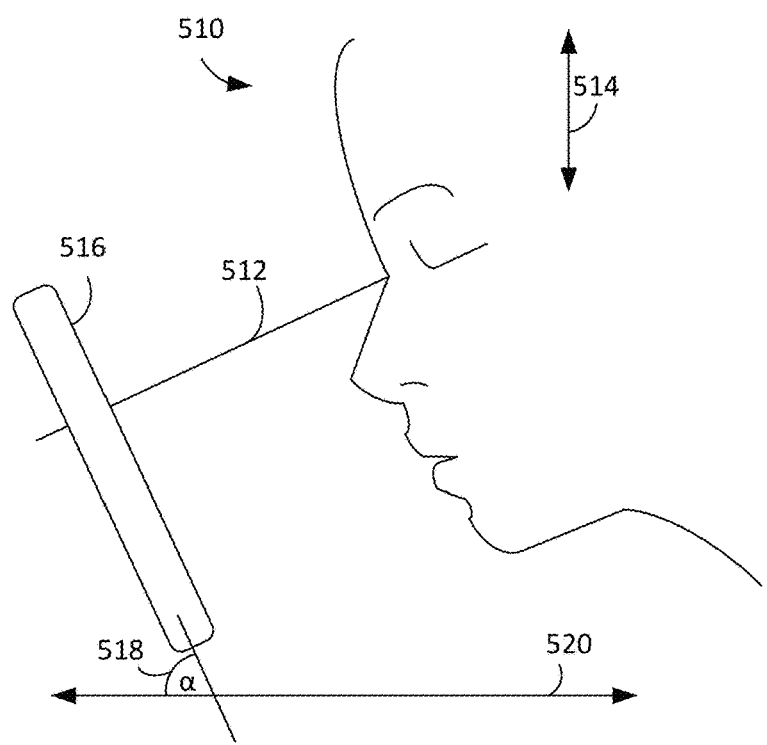
FIG. 5B is schematic of aspects of the functionality of the system.

Referring to FIG. 5B, the mobile device 516 is held at less desirable angle 518 from the horizontal plane 520. While the mobile device 516 is generally at a 90-degree angle to the user's gaze 512, the position of the user's head is undesirable. The user 510 is shown with a disadvantageous position wherein the head is both forward and flexed when compared with the vertical plane 514. This is not optimal spinal alignment. This angle would cause the triggering mechanism of the operating system to send a user notification. The user notification may be varied in duration or intensity according to the size of stress angle 518.

Figure 6A:
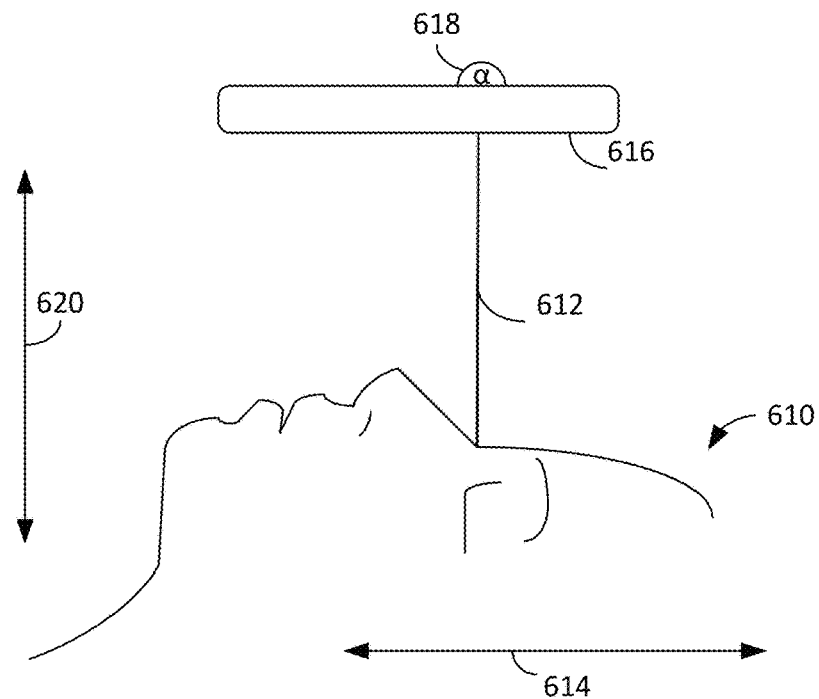
FIG. 6A is schematic of aspects of the functionality of the system.

Referring to FIG. 6A, user 610 aligns the head horizontally as if the user is reclining as in lying on the floor. The line of sight 612 (e.g., user's gaze) is generally parallel to plane 620. This position places the head at about a 180-degree angle horizontally as compared with plane 614. The mobile device 616 is advantageously held at about a 180-degree angle (e.g., approximately parallel) to horizontal as shown by angle 618.

Figure 6B:
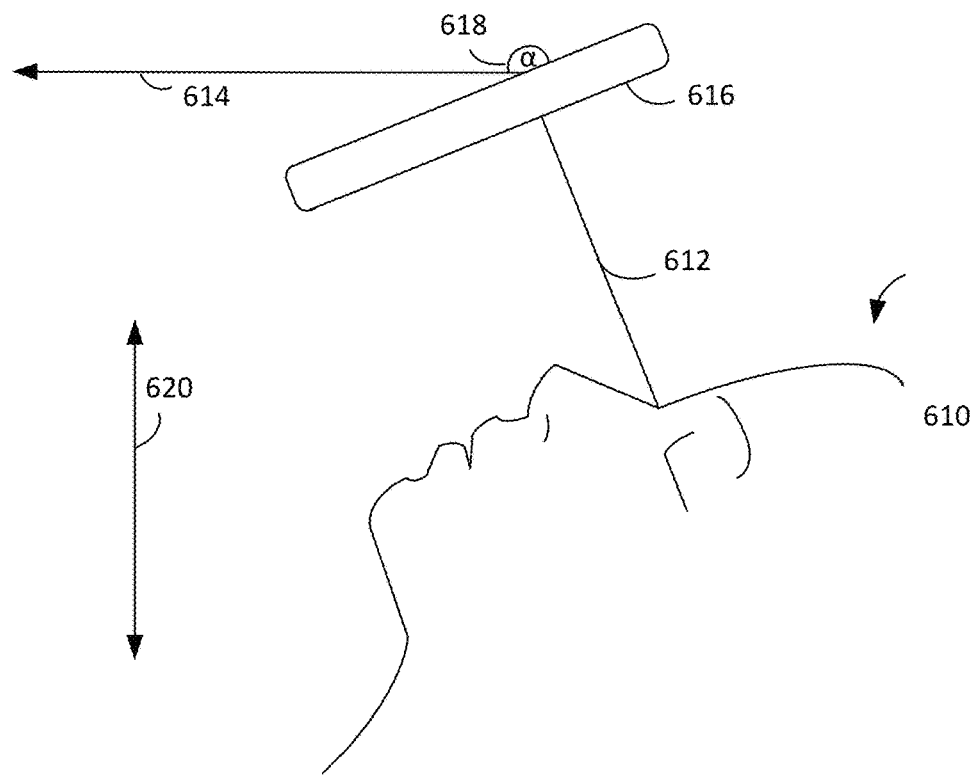
FIG. 6B is schematic of aspects of the functionality of the system.

Referring to FIG. 6B, the mobile device 616 is held at an angle 618 from the horizontal plane 614 that is less desirable. While the mobile device 616 is generally at a 90-degree angle to the user's gaze 612, the position of the user's head is undesirable. The user 610 is shown with a disadvantageous position wherein the head is both forward and flexed when compared to the horizontal plane 614. This is not optimal spine alignment when the user is laying down. This angle would cause the triggering mechanism of the operating system to send a user notification. The user notification may be varied in duration or intensity according to the size of stress angle 618.

Figure 7:
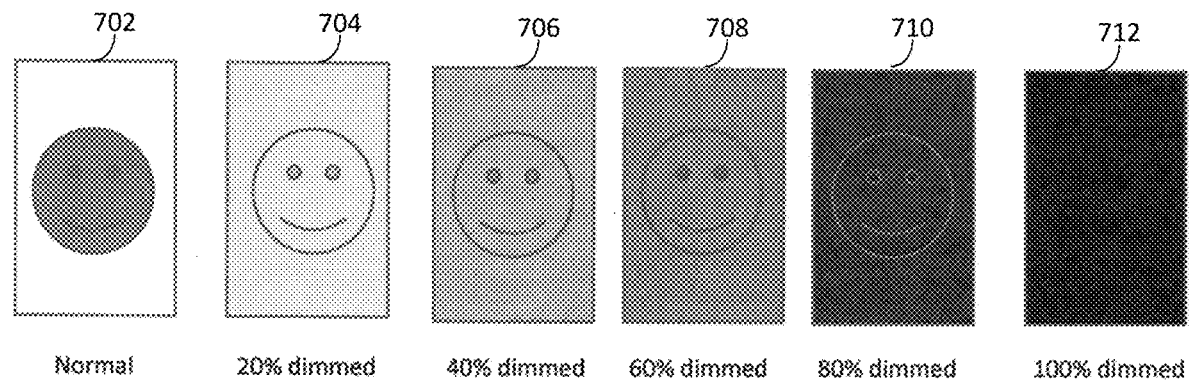
FIG. 7 is a schematic of aspects of the system.

Referring to FIG. 7, the screen can be dimmed progressively according to the number of iterations of unacceptable inputs such as angles. For example, the user tilts the mobile device to an unacceptable angle multiple times in a given time period. In this case, each time the mobile device is placed in an unacceptable angle, the screen can be dimmed at a higher percentage than the previous time or for a longer time than the previous time or both. The screen dimming intensity may also be determined according to the size of the stress angle Screen 702 shows the user defined brightness when the device is held properly, Screen 704 shows the screen being dimmed by 20%. Screen 706 shows a 40% dimming effect. Screen 708 shows a 60% dimming effect. Screen 710 shows an 80% dimming effect. Screen 712 shows a 100% dimming effect. The dimming effect can be any increment between shutting off the display to no effect.

Figure 8:
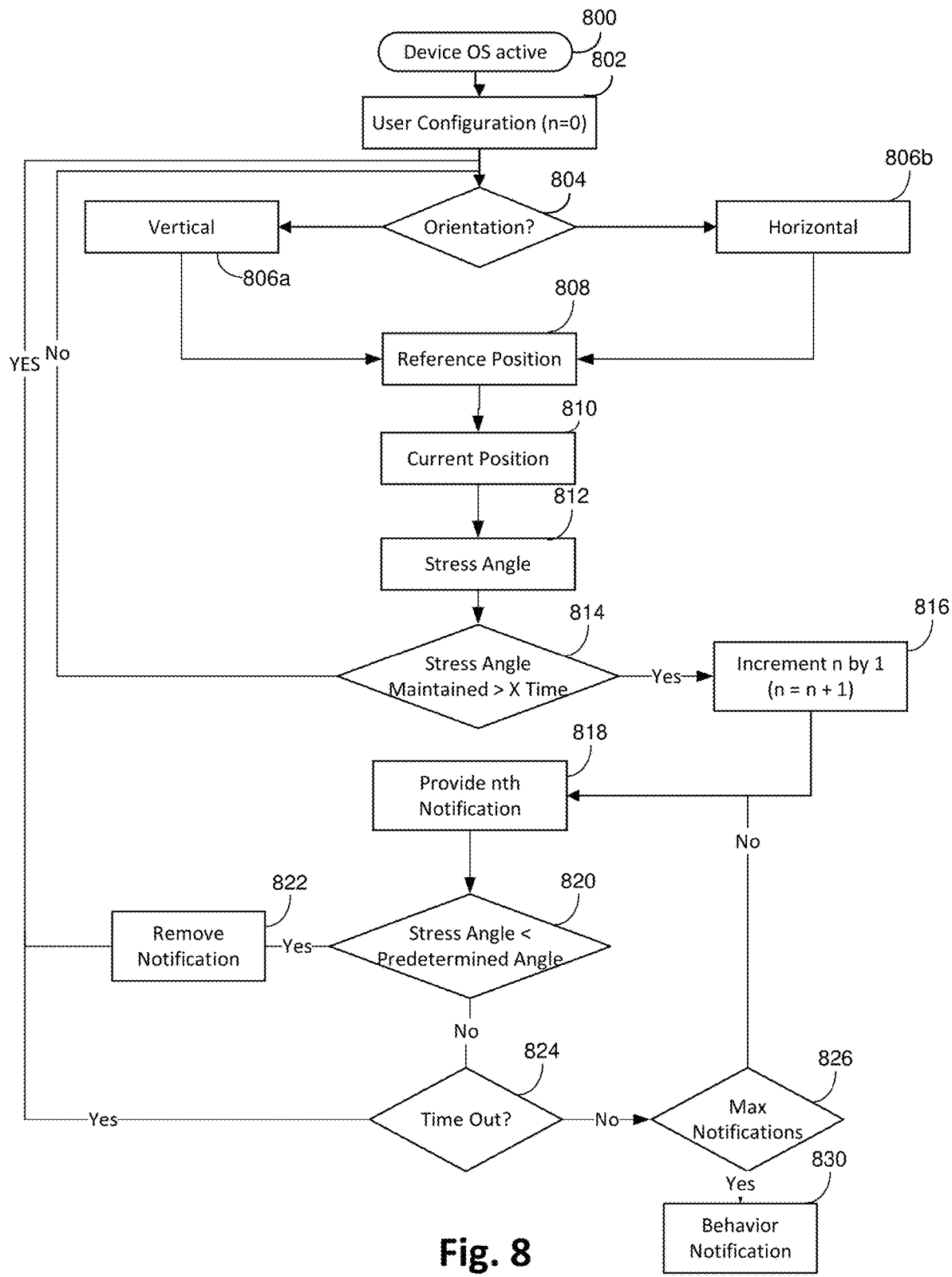
FIG. 8 is a flowchart illustrating certain functionality of system.

Referring to FIG. 8, one embodiment of the processes and procedures implemented with hardware and the operating system and modifications to an operating system. The operation of the system can begin with activation 800. User configuration information can be retrieved at 802 and can include setting an initial iteration counter to zero (e.g., n=0). The initial orientation of the hardware device (e.g., smart phone) can be determined at 804. The initial orientation can be classified into vertical or horizontal in one embodiment as shown in 806a and 806b respectively. According to the orientation, a reference position can be determined at 808. The reference position can be the preferred position where the portable device is positioned by the user and can be the position that minimizes or eliminates a stress angle. The position of the portable device can be determined at 810 which can be used to determine stress angle at 812. The stress angle can be the difference between the reference position and the current position. In one embodiment, when the stress angle exceeds a predetermined value, a notification can be generated by the operating system of the portable device.

In one embodiment, when the stress angle exceeds the predetermined value for length of time "X" at 814, the operating system can generate a notification. In this embodiment, notifications are generated upon prolonged periods of time when the stress angle exceeds a predetermined value rather than when the stress angle exceeds the predetermined value in passing or for small amounts of time.

In one embodiment, the operating system can increment a count of notifications at 814 and can activate a user notification at 818 to provide the user with a notification. In one embodiment the notification is achieved by dimming the screen, but such notification may also include obscuring the screen, flashing the screen or other light of the mobile device, emit an audible signal, actuate a haptic assembly (e.g., vibrate or other feedback), as well as any combination. The user notification can be activated by the operating system that communicates with the mobile device hardware to change the appearance of the screen. The appearance of the screen can be modified through the operating system and can control the hardware directly such as drivers that are in communication with an operating system layer. This notification informs the user that the motion or position of the device should be changed or is undesirable.

When a notification occurs, the operating system can determine if the user modifies the motion or position of the device so that the stress angle is less than the predetermined angle at 820. If so, the notification is removed. In one embodiment, the stress angle needs to be less than the predetermined angle for a period of time before the notification is removed.

The operating system can detect and record such modification including the date, time, duration, and time from notification to modification, characteristics of the modification and any combination. For example, the user can tilt the mobile device upward (typically straightening the neck) in response to the notification. Upon detecting modification of the position of the device for a sufficient period of time and specific duration, in one embodiment the operating system can remove the user notification at 822. In one embodiment, the operating system can determine that the stress angle exceeds the predetermined angle for an excessive period (e.g., times out) at 824 and reset the process.

In one embodiment, the operating system can rely upon a recovery period which can represent the time interval necessary for the muscles to recover, ligaments to relax, and the body to generally recover from a stress angle. If the user continues to hold the device in a position that exceeds the predetermined angle for a user configured predetermined length of time (e.g., threshold time), the operating system can take further action such as increasing the magnitude or intensive of the notification, locking the mobile device, or other notifications designed to modify the user's behavior.

If the device is still positioned at a stress angle, the operating system can determine if a maximum number of cycles have been reached at 826. The preset maximum number of cycles may be any number including infinity where there is no maximum. If the maximum number of cycles has not been exceeded, a new cycle is started incrementing the notification count and continuing in cycle back to the cycle number determination. The cycle can be repeated with subsequent user notifications given until either the removal of notification occurs upon modification of the device position and the sequence is reset or the maximum number of cycles is reached at 826. When the maximum number of cycles is reached at 826, the system can take a behavior modification action at 808 before restoring the device path 812. The behavior modification action at 830 may require restoration to an acceptable angle relative to the reference position for a predetermined period of time to remove the effects of prior notifications. Alternatively, behavior modification action may simply be disabling the device for a period of time, limiting functionality of the device, disabling one or more applications on the device, or any similar action. The behavior modification action may be ended by passage of time, returning the device to an acceptable position, cycling the power of the device, or other such action. Such functionality requires a time determining system comprising a means to record initial tilt exceeding the predetermined angle, a means to record duration of time during which the tilt of the device exceeds the predetermined angle, a means to reset the duration when the tilt is returned to an angle within the predetermined angle, and a means to prompt user notification and reset the duration.

In the description, numerous details are set forth for purposes of explanation in order to provide a thorough understanding of the present invention. However, it will be apparent to one skilled in the art that not all of these specific details are required in order to practice the present invention. It is also noted that the invention may be described as a process, which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged.

As is known in the art, the operations described above can be performed by hardware, software, or some combination of software and hardware. Various aspects of embodiments of the invention may be implemented using circuits and logic devices (hardware), while other aspects may be implemented using instructions stored on a machine-readable medium (software), which if executed by a processor, would cause the processor to perform a method to carry out embodiments of the invention. Furthermore, some embodiments of the invention may be performed solely in hardware, whereas other embodiments may be performed solely in software. Moreover, the various functions described can be performed in a single unit, or can be spread across a number of components in any number of ways. When performed by software, the methods may be executed by a processor, based on instructions stored on a computer-readable medium. If desired, the instructions can be stored on the medium in a compressed and/or encrypted format.

It is understood that the above descriptions and illustrations are intended to be illustrative and not restrictive. It is to be understood that changes and variations may be made without departing from the spirit or scope of the following claims. Other embodiments as well as many applications besides the examples provided will be apparent to those of skill in the art upon reading the above description. The scope of the invention should therefore be determined, not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventor did not consider such subject matter to be part of the disclosed inventive subject matter.

What is claimed is:

1. A system for implementing behavior modification while using a mobile device comprising:
    a mobile device having a computer readable storage and a display;
    a processor included in the mobile device and in communication with the computer readable storage; and,
    instructions stored on the computer readable storage that when executed by the processor cause the mobile device to:
        determine a current position of the display;
        determine a reference position relative to one of a vertical position and a horizontal position,
        determine a tilt angle of the display according to a difference between the current position and the reference position, and,
        actuate a user notification according to a determination that the tilt angle of the display exceeds a predetermined angle, wherein the user notification is activated for an activation period of time and wherein the activation period of time is increased according to a number of times the tilt angle of the display exceeds the predetermined angle.

2. The system of claim 1, including a time determining system that is adapted to determine a length of time that the display is held in the current position and wherein the user notification is actuated according to a determination that the tilt angle of the display exceeds a predetermined angle for a predetermined length of time.

3. The system of claim 2, wherein the predetermined length of time is reduced according to a number of times the tilt angle of the display exceeds the predetermined angle.

4. The system of claim 1, wherein the activation period of time is increased according to the size of the angle at which the tilt angle of the display exceeds the predetermined angle.

5. A system for implementing behavior modification while using a mobile device comprising:
    a mobile device having a computer readable storage and a display;
    a processor included in the mobile device and in electrical communication with the computer readable storage;
    instructions stored on the computer readable storage that are executed by the processor in response to the mobile device being powered on and cause the mobile device to:
        determine a current position of the display,
        determine a reference position relative to one of a vertical position and a horizontal position, and,
        determine a tilt angle of the display, wherein the tilt angle is the difference between the current position of the display and the reference position, and,
        actuate a user notification according to the tilt angle exceeding a predetermined angle, wherein the user notification is actuated at a predetermined disturbance intensity level and the disturbance intensity level is increased according to the size of the angle by which the tilt angle of the display exceeds the predetermined angle.

6. The system of claim 5, wherein the disturbance intensity level is increased according to a number of times the tilt angle of the display exceeds the predetermined angle.

7. The system of claim 5, including a time determining system that is adapted to determine a length of time that the display is held in the current position and wherein the disturbance intensity level is increased according the length of time that the device tilt angle of the display exceeds the predetermined angle.

8. The system of claim 5, wherein the user notification is sent to an executing application on the mobile device wherein the executing application is adapted to suspend an operation of an application running on the mobile device.

9. A system for implementing behavior modification while using a mobile device comprising:

a mobile device having a computer readable storage and a display;

a processor included in the mobile device and in electrical communication with the computer readable storage;

instructions stored on the computer readable storage that, when executed by the processor cause the mobile device, upon activation of the display, to:

determine a current position of the display, determine a reference position relative to one of a vertical position and a horizontal position, determine a tilt angle of the display according to a difference between the current position of the display and the reference position, actuate a user notification according to a determination that the tilt angle of the display exceeds a predetermined angle, and stop the user notification upon detection that the tilt angle of the display no longer exceeds the predetermined angle.

10. The system of claim 9 further including a time determining system that is adapted to determine a length of time that the display is held in the current position and wherein the user notification is actuated according to a determination that the tilt angle of the display exceeds a predetermined angle for a predetermined length of time.

11. The system of claim 10, wherein the predetermined length of time is reduced according to a number of times the tilt angle of the display exceeds the predetermined angle.

12. The system of claim 9, wherein the activation period of time is increased according to a number of times the tilt angle of the display exceeds the predetermined angle.

13. The system of claim 9, wherein the activation period of time is increased according to the size of the angle at which the tilt angle of the display exceeds the predetermined angle.

14. The system of claim 9, the disturbance intensity level is increased according to one of a number of times the tilt angle of the display exceeds the predetermined angle, the size of the angle by which the tilt angle of the display exceeds the predetermined angle and the length of time that the tilt angle of the display exceeds the predetermined angle.

15. The system of claim 9 wherein the instructions further cause the mobile device to determine the tilt angle of the display upon detection of a movement of the display.

* * * * *